(12) United States Patent
Bernini et al.

(10) Patent No.: US 10,716,504 B2
(45) Date of Patent: Jul. 21, 2020

(54) MEDICAL SYSTEM HAVING PLUG AND PLAY FUNCTION

(71) Applicant: Roche Diabetes Care, Inc., Indianapolis, IN (US)

(72) Inventors: Nicole Bernini, Burgdorf (CH); Harvey B. Buck, Jr., Indianapolis, IN (US); Andreas Eberhart, Baar (CH); Sybille Froech, Mannheim (DE); Otto Gaa, Worms (DE); Michael Marquant, Mannheim (DE); Juergen Rasch-Menges, Schwetzingen (DE); Bernd Roesicke, Mannheim (DE); Joerg Scherer, Aalen (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 326 days.

(21) Appl. No.: 15/688,317

(22) Filed: Aug. 28, 2017

(65) Prior Publication Data
US 2017/0357766 A1    Dec. 14, 2017

Related U.S. Application Data

(60) Division of application No. 14/820,980, filed on Aug. 7, 2015, now Pat. No. 9,773,093, which is a
(Continued)

(30) Foreign Application Priority Data

Mar. 23, 2009   (EP) .................................. 091558924

(51) Int. Cl.
*A61B 5/00* (2006.01)
*A61B 5/145* (2006.01)
(Continued)

(52) U.S. Cl.
CPC .......... *A61B 5/4839* (2013.01); *A61B 5/0015* (2013.01); *A61B 5/0024* (2013.01);
(Continued)

(58) Field of Classification Search
CPC . A61B 5/0015; A61B 5/0031; A61B 5/14532; A61B 5/14503; A61B 2560/0406; A61B 2560/045
See application file for complete search history.

(56) References Cited

U.S. PATENT DOCUMENTS

| 5,690,119 A | 11/1997 | Rytky et al. |
| 6,150,951 A | 11/2000 | Olejniczak |

(Continued)

FOREIGN PATENT DOCUMENTS

| DE | 10221179 A1 | 12/2003 |
| DE | 102007033673 A1 | 1/2009 |
| WO | WO-03/094708 A1 | 11/2003 |

OTHER PUBLICATIONS

Schrenker et al., "Building the Foundation for Medical Device Plug-and-Play Interoperability." Apr. 1, 2001.

*Primary Examiner* — Eric F Winakur
(74) *Attorney, Agent, or Firm* — Harness Dickey

(57) ABSTRACT

A medical system is disclosed, which can be useable in particular for monitoring and/or controlling at least one bodily function of a user. The medical system comprises a control device and at least one medical user element embodied separately from the control device. The medical user element and the control device are designed to exchange data wirelessly. The medical system is designed to enable an automatic assignment step, wherein an exchange of personal data between the medical user element and the control device is enabled by the automatic assignment step. The medical system is furthermore designed to automatically initiate the automatic assignment step by means of an
(Continued)

assignment coupling between the medical user element and the control device. The medical system is furthermore designed to enable a separation of the assignment coupling for medical operation of the medical system after the assignment step.

19 Claims, 5 Drawing Sheets

Related U.S. Application Data continuation of application No. 13/240,092, filed on Sep. 22, 2011, now Pat. No. 9,101,306, which is a continuation of application No. PCT/EP2010/053459, filed on Mar. 17, 2010.

(51) Int. Cl.

| | |
|---|---|
| A61N 1/372 | (2006.01) |
| A61B 5/117 | (2016.01) |
| G06F 21/44 | (2013.01) |
| G06F 21/32 | (2013.01) |
| A61B 90/98 | (2016.01) |
| G16H 40/63 | (2018.01) |
| H04W 4/80 | (2018.01) |
| H04W 4/70 | (2018.01) |
| G06F 19/00 | (2018.01) |
| H04L 29/08 | (2006.01) |

(52) U.S. Cl.
CPC ........ *A61B 5/0031* (2013.01); *A61B 5/14503* (2013.01); *A61B 5/14532* (2013.01); *A61B 5/14546* (2013.01); *A61B 5/7271* (2013.01); *A61B 5/74* (2013.01); *A61B 90/98* (2016.02); *G06F 19/00* (2013.01); *G06F 21/32* (2013.01); *G06F 21/445* (2013.01); *G16H 40/63* (2018.01); *H04W 4/70* (2018.02); *H04W 4/80* (2018.02); *A61B 2560/045* (2013.01); *A61B 2560/0406* (2013.01); *A61N 1/37235* (2013.01); *H04L 67/12* (2013.01)

(56) References Cited

U.S. PATENT DOCUMENTS

| | | | |
|---|---|---|---|
| 6,621,890 | B1 | 9/2003 | Rondeux |
| 6,738,670 | B1 | 5/2004 | Almendinger et al. |
| 6,752,155 | B2 | 6/2004 | Behm |
| 8,225,015 | B2 | 7/2012 | Gao-Saari et al. |
| 8,745,247 | B1 | 6/2014 | Park et al. |
| 2004/0064166 | A1 | 4/2004 | Thompson et al. |
| 2005/0054289 | A1 | 3/2005 | Salazar et al. |
| 2005/0113886 | A1 | 5/2005 | Fischell et al. |
| 2008/0319296 | A1 | 12/2008 | Bernstein et al. |
| 2009/0036750 | A1 | 2/2009 | Weinstein et al. |
| 2012/0116190 | A1 | 5/2012 | Iketani et al. |

MEDICAL SYSTEM HAVING PLUG AND PLAY FUNCTION

REFERENCE

This application is a divisional of U.S. patent application Ser. No. 14/820,980 filed Aug. 7, 2015 which is a continuation of U.S. patent application Ser. No. 13/240,092 filed Sep. 22, 2011, which is a continuation of PCT/EP2010/053459 filed Mar. 17, 2010, which is based on and claims priority to European Patent Application No. EP 09 155 892.4 filed Mar. 23, 2009, which are hereby incorporated by reference.

FIELD

This disclosure relates to a medical system comprising a control device and at least one medical user element embodied separately from the control device, and also to a method for operating the medical system. Medical systems and methods of this type are used in particular for monitoring and/or controlling at least one bodily function of a user, for example for continuously monitoring an analyte concentration in a body fluid. Fields of use can be found in particular in the hospital area, in the care area or in the area of home care and/or of home monitoring. However, other fields of use are also possible, in principle.

BACKGROUND

Numerous examples of medical systems having a plurality of components embodied separately from one another which are intended to communicate with one another are known from medical technology. The plurality of components comprise at least one medical user element and at least one control device. The user element can be a personal medical element, for example having a measurement function and/or a medication function. User elements of this type are generally driven and/or read by at least one control device. The control device can provide a user interface, for example, by means of which a user (for example a patient or a healthy person) can control the system or can interrogate information of the system. Examples of medical systems of this type are presented in US 2005/0113886A1 Implantable medical system with long range telemetry by Fischell et al. (May 26, 2005); U.S. Pat. No. 6,738,670B Implantable medical device telemetry processor by Almendinger et al. (May 18, 2004); and U.S. Pat. No. 6,752,155B2 Tactile feedback for indicating validity of communications link with an implantable medical device by Behm (Jun. 22, 2004).

A challenge in the case of medical systems of this type consists in the connection of the individual components of these systems. In this case a wireless data connection, that is to say a connection in which a data exchange is made possible in the first place not via artificial lines (such as, for example, cables, interfaces or plugs), rather the data exchange takes place by means of electromagnetic waves, is often preferable to a wire-based data exchange for reasons of practicability. In the case of a wireless data exchange, however, in medical systems the particular challenge consists in the fact that, on the one hand, an interoperability of the individual components has to be ensured without a user (for example a patient of childhood age or older persons) having to perform complex technical measures for this purpose. On the other hand, it is necessary to ensure that sensitive personal data such as control commands which are communicated to a user element or measurement data which are communicated to the control device by the user element reach the correct addressee. Thus, in particular, the operability, which can be understood to mean a plug-and-play interoperability, for example, must not be implemented so widely that new devices are automatically integrated into the medical systems which are not intended to belong to the latter, such as user elements of other users, for example. In this case, plug-and-play concepts are generally understood to mean concepts in which new hardware components can be added to systems and are recognized by the system, without a separate driver having to be loaded for this purpose. This can lead, for example, to personal measurement data being revealed in an undesirable manner, or even to the erroneous addressing of control commands, with possibly fatal medical consequences. For this purpose, standards which serve this purpose and which are combined under IEEE 11073, for example, are already known from medical technology.

A particular difficulty is posed in the case of medical systems which have at least one diagnostic function, for example in diagnostic measuring systems. Examples of such medical systems are so-called continuous monitoring glucose systems, which are already commercially available at the present time. In this case, in current systems, the individual components, such as, for example, disposables, re-usables and also read-out and data management components, are generally sold together in a set. However, it is also possible for system parts to be procured subsequently and put into operation later. In this case, the individual components are individually put into operation and, if appropriate, coordinated with one another or allocated to one another by the user.

Particularly in the case of diabetes self-monitoring systems, but also in the case of other diagnostic measuring systems, consumable materials are generally used, such as sensors, for example. Said sensors carry in part complex, specific information which they have to convey to the target system, for example a control device, during use. On the other hand, collected data records are generally sent to peripheral computer systems for more extensive conditioning or processing. Such activities generally require a high degree of organization and coordination by the operator.

Particularly in diagnostic measuring systems of this type, but also in differently configured medical systems and primarily with the advent of new multi-sensor systems (for example body area networks, BANs), the development of a plug-and-play technology has hitherto either still not been introduced at all or been developed only insufficiently. In many cases this has the effect that users, who are generally not educated in the technological field, have difficulties in dealing with the complex technology unless the users are guided and trained in a manner involving a high outlay. However, such guidance and training requires extensive efforts on the part of the system supplier with regard to the configuration of user manuals or training measures.

In many cases there is a further problem with consumable materials, such as, for example, test strips or other types of sensors. Here, for process-technological reasons, in many cases it is necessary to determine calibration data and convey them to the consumable material in the form of a separate data carrier. These data have to be transmitted to the measuring or evaluation device when the consumable material is started up, such that said device can, if appropriate, carry out a correction of the measurement values determined. In many cases, however, data and consumable material are not necessarily assigned physically to one another, such that the consumable material and the data can be mixed up upon the re-initialization of system components, but to an increased extent also when newly equipping a system with consumable material. This can lead to incorrect measurement results and possibly serious medical consequences.

Furthermore, problems can occur in components that communicate by radio technology. As explained above, such connections between the individual components are not unambiguously defined and not unambiguously visible, as is possible particularly in the case of networked connections or connections connected by cables or optical links. Radio connections are possible for example through or across natural obstacles such as walls or the like. Many modern radio networks are set up by definition on their own authority by virtue of potential network components independently identifying themselves and providing possible data exchange. This means that components of the networks can communicate with one another without the user having to intervene actively for this purpose. In this case, however, generally no specific user data, that is to say private data, in particular, are exchanged yet. If such personal or private data are intended to be transmitted, then generally a so-called authentication has to be carried out beforehand. This can be effected for example by a manual inputting of numbers and/or codes directly into the relevant components which are intended to communicate with one another. What is problematic about this authentication, however, is that it presupposes an active and complex activity on the part of the user, which can be susceptible to errors particularly in the case of use by older patients or children. Thus, particularly in the case of long series of numbers being input, which is associated with a considerable complexity anyway, incorrect inputs can easily occur, which in turn can lead to malfunctions of the system.

These malfunctions increase the risk for medical networks, which can be beset with a risk anyway for example on account of numerous possibilities for incorrect operation. Thus, by way of example, the insertion of consumable material and of auxiliary materials such as batteries or memory components, for example, by a user can be associated with incorrect operation, for example polarity reversal or incorrect contact-making. This can lead to malfunctions and damage in the medical network. Generally, therefore, the start-up of individual system components or entire networks necessitates comprehensive, often difficult to understand documentation, which causes costs, requires space and generally is not noticed or read by the user at all, or only in an error situation.

Therefore, it is desirable to provide a medical system which at least substantially avoids the disadvantages of known medical systems. In particular, the medical system should be able to independently identify new system components, in particular new medical consumable materials, and to integrate them securely and reliably with the least possible effort for the user.

SUMMARY

A medical system should be understood generally to mean a system which comprises at least two components which, in particular, can be configured spatially separately from one another and which has at least one medical, in particular therapeutic and/or diagnostic, function. In particular, the system can be one which serves for monitoring and/or controlling at least one bodily function of a user. In this case, a bodily function should generally be understood to mean, in principle, any desired function and/or property of the body of the human or animal user, for example a physically and/or chemically measurable property such as e.g. an analyte concentration in a body fluid and/or a bodily function which is associated with an actuator system, for example a valve function, a muscle function or a discharge of specific chemical substances. Various examples are discussed in greater detail below. The user can be, in principle, a patient, but also, in principle, healthy persons. In this case, at least one component of the medical system, in particular the user element discussed in greater detail below, is preferably intended to be carried by the very user whose bodily function is intended to be monitored and/or controlled, preferably directly on or in the body.

The medical system comprises a control device. Although many medical systems comprise only a single control device, some medical system can comprise a plurality of control devices of this type, which can likewise communicate. The control device can be configured in portable fashion, in particular, such that it can be carried by the actual user. Accordingly, the control device can be dimensioned in terms of its dimensions in order to be carried for example in a user's pocket.

In this case, a control device should be understood to mean, in principle, a device which has at least one user interface via which a user—in some embodiments without the aid of further electronic components—can input data and/or commands into the medical system and/or can read out information from the medical system. By way of example, the control device can comprise for this purpose one or more operating elements, for example one or more keys, one or more touch screens, voice inputs, track balls, slides, levers, dials, scanners or other types of operating elements or combinations of the stated or other types of operating elements. Furthermore, the control device, alternatively or additionally, can comprise one or more indicator elements, for example in order to communicate information to the user optically and/or acoustically and/or tactically (for example by vibrations). By way of example, it can comprise at least one indicator element in the form of a display, for example a segmented display and/or a matrix display. The latter can also be combined with operating elements, for example in the form of a touch screen.

The control device can comprise a simple blood glucose measuring device and/or also one or more devices originating from non-medical areas, such as, for example, mobile radio devices, PDAs or lifestyle or sports devices, such as, for example, pedometers, pulse meters or the like. The control device should therefore be designed to enable a user to input commands into the medical system, in particular for controlling the medical user element explained in even greater detail below, and/or for reading out information, for example measurement data of the medical user element, via the control device.

The medical system furthermore has at least one medical user element embodied separately from the control device. A medical user element should be understood to mean any desired device having a medical function which can be carried by the user. This carrying can take place directly on or in the body. The medical function can comprise, in particular, a therapeutic and/or a diagnostic function. By way of example, this function can comprise a measurement function for detecting specific data, in particular for detecting data which are characteristic of the user, for example data which are associated with a bodily function. By way of example, they can be measurement data of an analyte concentration in a body fluid of the user. Alternatively or additionally, the medical function can comprise a medication function, for example an administration of a specific medicament at specific points in time and/or in predefined amounts and/or concentrations. By way of example, the function of an insulin pump can be involved. Once again alternatively or additionally, the medical function can also comprise an actuator function, for example a pacemaker function and/or a valve function. Various examples are explained in greater detail below. The medical user element can comprise at least one consumable element since the advantages of the medical system as described below are manifested positively in particular when consumables are exchanged.

The medical user element and the control device are designed to exchange data wirelessly. In this case, the term data can generally subsume information and/or commands, for example measurement data and/or control commands. In this case, a wireless data exchange should be understood to mean a data exchange in which data processing does not have to be set up by the user by means of specific hardware, such as a cable, for example; rather, the wireless data exchange is preferably intended to take place by means of electromagnetic waves and/or conductive guide mechanisms which are transmitted directly or else, for example, via a body network including body parts of the user as conducting elements. The wireless data exchange can comprise a data exchange via radio, preferably a data exchange in which the control device and the medical user element do not have to be arranged in a specific orientation with respect to one another, such as, for example, in the case of an infrared data connection. In principle, however, other types of wireless data exchange can also be implemented, for example conductance on/in the body or capacitive, dielectric displacement currents, for example in the form of so-called body area networks (BANs). Data exchange can be via a radio connection, such as a far-field radio connection.

The medical system is designed to enable an automatic assignment step, which enables personal data to be exchanged between the medical user element and the control device. In this context, automatic should be understood to mean, in particular, that the assignment step can take place without complex user actions, for example without the inputting of complex alphanumerical codes, without the exchange of memory chips or similar data carriers, by the user. The assignment step is therefore a method step that enables a communication between the control device and the medical user element in which even sensitive, personal data can be exchanged. Before the at least one assignment step is actually carried out, the medical user element and the control device can communicate, for example by virtue of a simple recognition signal being communicated, which signals purely the presence of the user element in the vicinity of the control device, or vice versa. In this way, before the assignment step, for example, a provisional communication can take place by means of which, for example, general data can be exchanged. In principle, this provisional communication can optionally also extend to an extended interoperability. An extended interoperability (IO) can be understood to mean the software protocol level in a basic technology, for example Bluetooth, for example having a fixed carrier frequency, e.g. 2.45 GHz. However, interoperability could also be extended in such a way that the hardware can also be automatically adapted. By way of example, a radio carrier frequency can be automatically adapted. By way of example, a changeover can take place from Bluetooth to 1.9 GHz GSM mobile radio or to 433 MHz of a different so-called ISM band. These examples show that, in principle, there are a large number of possibilities for configuring a provisional communication in which no personal data are exchanged yet.

Personal data, the exchange of which is intended to be possible only after the assignment step has been carried out successfully, should be understood generally to mean data and/or control commands which are essential for the functionality of the medical system, for example for a therapeutic and/or diagnostic function of a specific medical user element. They can be, for example, measurement data which were detected at this specific user using the medical system and/or the specific medical user element, and/or control commands which are intended for a specific medical user element and which are not intended to be communicated to other medical user elements. The classification of data as personal data can be defined for example in one or more components of the medical system, for example in the control device and/or in the medical user element. By way of example, the control device can be designed in such a way that specific control commands are classified in it as personal data which are permitted to be communicated, only after the assignment step has been carried out successfully, to a specific user element with which the assignment step was carried out. Conversely, by way of example, it is possible to classify specific measurement data or types of measurement data in a medical user element as personal data, such that these measurement data can be communicated to the control device for example only when an assignment step has been successfully ended with this specific control device.

The exchange of the personal data between the medical user element and the control device can be effected unidirectionally in one of the two directions, that is to say, for example, from the control device to the medical user element or vice versa, or bi-directionally. Thus, it is possible to communicate measurement data from the medical user element to the control device and control commands from the control device to the medical user element. However, other configurations are also possible.

The medical system is designed according to the invention to automatically initiate the automatic assignment step by means of an assignment coupling between the medical user element and the control device. This means that the assignment step is successful if the medical system, preferably both the control device and the medical user element, recognizes that the assignment coupling has been produced. In this case, as will be explained in even greater detail below, an assignment coupling should be understood to mean a predefined handling of the control device and of the medical user element by the actual user and/or some other person which differs from a handling in normal operation, for example medical operation, in which the medical system regularly operates and in which the personal data are exchanged. In other words, the assignment coupling is intended to comprise a deliberate handling of the medical user element and of the control device by the user and/or some other person which does not occur randomly or occurs randomly only with very low probability in medical operation and by means of which the assignment step is initiated. Said assignment coupling is typically intended not to comprise any complex handling at all, such as, for example, the exchange of memory elements or the inputting of alphanumeric characters.

The conditions under which an assignment takes places can be fixedly predefined. Said conditions can comprise, as specified above, for example the fixedly predefined assignment coupling. Alternatively or additionally, the conditions under which the assignment takes place, that is to say the conditions for an automatic assignment step, can also be configured in variable fashion. By way of example, said conditions under which an assignment takes place, and which can also be designated as "pairing conditions", can be dependent on external circumstances and/or a state of the user. If a critical state is detected, for example hypoglycemia, then it is possible for the medical user element to be designed to enable a facilitated assignment with one or more control devices, for example one or more additional control devices. By way of example, upon detection of a critical state, the user element can be designed automatically to communicate with any control device in its vicinity which meets specific conditions and is in a "physician mode" and also to exchange personal data.

The medical system is furthermore designed to enable a separation of the assignment coupling for medical operation of the medical system after the assignment step, that is to say after the assignment step has been successfully carried out. This means that the assignment coupling is produced only temporarily, and can then subsequently be separated for medical operation. Consequently, in medical operation, in which the personal data are exchanged, the assignment coupling no longer exists; rather, preferably exclusively the exchange of the personal data takes place via the wireless data connection, in which case, however, by way of example, an assignment identification exchanged during the existence of the assignment coupling can continue to be used. In this case, medical operation should be understood to mean the normal operation of the medical system, for example diagnostic operation and/or therapeutic operation, for example measurement operation. In this operation, the medical data can be exchanged.

The medical system proposed thus enables, in a simple manner, plug-and-play operation in which new medical user elements can be integrated into the medical system or can be exchanged from said medical system. As a result of the assignment coupling that initiates the assignment step, an initiation of the exchange of personal data is possible in a simple and secure manner, without necessitating a complex handling by the user, such as, for example, the inputting of alphanumeric codes and/or the exchange of memory elements. However, such actions can additionally be provided.

The medical system thus enables the communication between the control device and the medical user element, wherein firstly the two components are connected to one another in a specific manner in the automatic assignment step, preferably without the user in this case having to input data or exchange a code or having to press keys. An authentication can take place automatically between the control device and the medical user element, such that a pairing between the control device and the medical user element can be brought about by the assignment step by means of the assignment coupling brought about deliberately by the user. The authentication, which enables personal data subsequently to be exchanged, can take place automatically between the components, such that a data exchange can subsequently take place without any further pairing process, in contrast to known medical systems. Thus, when a medical user element is started up, for example when a sensor is newly started up, an automatic assignment step in the form of an automatic pairing can take place, which enables the medical user element and/or the user to authenticate themselves.

Optionally, the medical system can also be configured in such a way that a user actually carries a code, for example on an RFID transponder. After a defined assignment coupling, that is to say after successful pairing, for example in accordance with one of the procedures described in even greater detail below, for example establishment of proximity, a pairing via a body area network, an active confirmation or the like, the medical system, for example the control device, then knows said code and can exchange data. A module can also know a plurality of codes of this type.

Certain embodiments of the medical system concern, in particular, the configuration of the assignment coupling. This assignment coupling, which enables an automatic pairing can comprise a deliberate action on the part of the user and/or some other person which is necessary for bringing about the assignment coupling and/or for initiating the assignment step. In certain embodiments, with regard to the performance of this action, no distinction is drawn between the cases where the treatment is performed by the actual user or by some other person, for example a physician, pharmacist or medical technician. These possibilities are intended to be encompassed by the term performance of the action by the user. The deliberate action is intended, in particular, as explained above, to be configured in a simple manner and with little susceptibility to errors and is intended to differ from other actions which occur in medical operation of the medical system or which could be carried out unwittingly. In particular, no inputting of alphanumeric characters by the user and/or exchange of memory elements and/or inputting of data and/or codes and/or actuation of keys should be necessary.

In a first possible configuration, the assignment coupling can comprise a temporary coupling alignment between the medical user element and the control device, wherein the coupling alignment is different than an alignment in medical operation and also than a random alignment of the components of the medical system. This coupling alignment can comprise a specific positioning and/or spatial orientation of the control device and of the medical user element with respect to one another. By way of example, this coupling alignment can comprise a specific spatial proximity, for example an undershooting of a minimum distance, through to a (non-random) physical contact between the medical user element and the control device. This obtaining of a spatial proximity for bringing about the coupling alignment can also be designated as "pairing by near closing". This coupling alignment can be configured in such a way that it does not occur during normal handling of the medical system, such that no random, undesired coupling alignment is possible. Examples of such a coupling alignment are presented below.

Alternatively or additionally, the assignment coupling can also comprise a temporary physical coupling connection between the medical user element and the control device, which can be brought about and subsequently disconnected again in a targeted manner by the user. This temporary physical coupling connection can be effected, for example, via a coupling interface, a docking station, a wire-based connection, a wireless near-field connection or an infrared connection. In contrast to the wireless connection for exchanging the personal data in medical operation, which can be effected in a manner not involving direct electrical coupling, in the case of this temporary physical coupling connection a temporary direct electrical coupling can also be effected, for example via a coupling cable, a coupling plug or the above mentioned docking station. Thus, the user element and the control device can be inserted into a docking station successively or simultaneously, such that, by means of this handling, the coupling connection is produced and the assignment step is initiated. The medical user element and the control device can be unambiguously assigned to one another.

In this case, a docking station should be understood to mean, in principle, a stationary device which can have, for example, a stationary power supply and/or also a dedicated, portable power supply, which makes it possible, for example, to exchange authentication information between the medical user element and the control device and/or to exchange assignment identifications in another way. A portable configuration of the docking station is also possible, in principle. Devices for transport and/or for energy supply, for example in the form of a charging part, of the medical user element and/or of the control device can also be wholly or partly embodied as a docking station and/or be contained in a docking station.

As an alternative or in addition to the docking station, a temporary wire-based connection can also be produced, for example by a user temporarily connecting the medical user element and the control device by means of a cable. An infrared connection can comprise a deliberate alignment of the medical user element relative to the control device by the user, such that infrared interfaces of these elements can in each case communicate with one another. Afterward, this infrared connection can be disconnected again, for example by the medical user element and the control device being positioned in such a way that an infrared communication can no longer take place.

Once again alternatively or additionally, the wireless near-field connection can comprise a connection via a radio frequency interface which only enables data to be exchanged over short distances, for example distances of a minimum distance or less, for example a few 10 cm. By way of example, transmission techniques typically used in RFID technology can be used, which, however, are not suitable subsequently for the exchange of personal data. By way of example, the medical user element can comprise an RFID chip and/or a transponder which can be read by a reader of the control device only in a specific coupling alignment between the medical user element and the control device, wherein the RFID connection can preferably subsequently be disconnected again. The subsequent exchange of personal data in medical operation then no longer takes place via the abovementioned RFID connection or near-field connection, but rather via the wireless connection described above. In this configuration or else in other configurations, both the medical user element and the control device should therefore have at least two interfaces, one interface for carrying out the automatic assignment step and one interface for the wireless data exchange of at least the personal data during medical operation.

As an alternative or in addition to the above mentioned possibilities, the assignment coupling can also comprise an indirect assignment coupling via at least one coupling element. In this case, the assignment coupling is intended to be configured in such a way that the medical user element and the control device can be temporarily connected to the coupling element simultaneously or successively in order to initiate the assignment step. In this case, a coupling element can be understood to mean, in principle, any desired article to which the medical user element and the control device can be connected simultaneously or successively, in particular in order to exchange one of a plurality of assignment identifications. In this way, the assignment in the assignment step, for example an authentication, can be effected indirectly via the coupling element. The coupling element can comprise and/or provide, for example, the temporary physical coupling connection described above. The coupling element can be for example an inanimate article, but can also comprise for example one or more body parts of the user via which signals can be exchanged, for example. As will be explained in greater detail below, biometric characteristic data in the form of biometric features can also be exchanged via a body part of the user or transmitted by the body part of the user simultaneously or successively both to the medical user element and to the control device, such that the medical user element and the control device can be assigned to one another.

The medical system can be designed to exchange at least one assignment identification via the assignment coupling (for example the coupling element mentioned above). This exchange can take place for example uni-directionally from the control device to the medical user element, or vice versa, or bi-directionally. Alternatively or additionally, the exchange can also comprise for example a third element, such as the above-mentioned coupling element, for example, which provides the assignment identification. In this case, both the control device and the medical user element have the corresponding or identical assignment identification, such that these two components can be unambiguously assigned to one another.

In this way, later a single data manager in the form of the control device can be provided, which can communicate in a targeted manner with any additional medical user elements, for example measuring devices, used by the patient, in such a way that firstly in the assignment step data in the form of the assignment identification are communicated to the data manager, which enable the latter to recognize in later normal data exchange processes during medical operation that said data originate from the specific medical user element or from the specific user of said medical user element. In this way, one and the same data manager can also interact with a plurality of medical user elements, wherein the exchanged data, for example the personal data, can always be unambiguously assigned to a specific medical user element. This greatly increases the handling security of the medical system, since firstly the control device can distinguish data of different medical user elements and since secondly an inadvertent linking of other medical user elements, for example of third-party users, into the medical system, for example a network of the medical system, can be avoided by means of the above mentioned assignment step. The control device can be designed to assign, in this medical operation, data, in particular personal data, communicated by the medical user element on the basis of the assignment identification to said medical user element and, for example, to perform corresponding further steps such as, for example, data evaluation, storage of the data or the like. However, a targeted linking of third-party persons who are deliberately authorized into one or more medical systems could also be effected, or a plurality of medical systems could be partly identical in respect of components. Thus, a control device could also be part of a plurality of medical systems which can be used separately. Thus, a plurality of users, for example a married couple, could use a common control device, for example a common data manager. The latter can then be used in a first medical system of a first user and in a second medical system of a second user. The first medical system and the second medical system can comprise different medical user elements. By means of the respective assignment identification, the current operation can then be assigned to a specific medical system, such that, for example, at any point in time at which personal data are exchanged, it is possible for the control device to recognize whether said personal data are to be assigned to the first medical system or to the second medical system. Accordingly, an evaluation and/or processing of the personal data can be effected separately, such that, for example, the different users can in each case only access their personal data and/or that confusion and/or mixing-up of the personal data is precluded.

A further advantageous configuration of the medical system concerns the assignment coupling already mentioned above, which enables the assignment step. As explained above, the assignment coupling can comprise a temporary, predefined coupling alignment between the medical user element and the control device. In some embodiments, it is desirable if said coupling alignment is supported by an external shaping of the medical system or of individual components of the medical system, such that, by way of example, a user unambiguously recognizes how the coupling alignment has to be effected. In this way, by means of an external shaping imparted to the medical system, it is possible to avoid an operating error when bringing about the coupling alignment. Accordingly, in some embodiments it is desirable if the medical user element and the control device are designed in terms of their external shape to enable a defined temporary coupling alignment between the medical user element and the control device. In some embodiments, the control device has a housing having at least one depression corresponding to an external shape of the medical user element. In this case, the medical user element, for the purpose of producing the assignment coupling, is intended to be able to be temporarily introduced into the depression. Alternatively or additionally, the housing can also be configured in a raised fashion, that is to say have at least one elevation, which can likewise correspond to the external shape of the medical user element, wherein the medical user element, for the purpose of producing the assignment coupling, can be applied to the elevation. The medical user element can accordingly have a pocket and/or a depression corresponding to the elevation. Generally, in a very broad definition of the terms "depression" and "elevation", the medical user element and the control device can have mutually corresponding male and female connecting elements which can be used for producing the assignment coupling. In this way, the control device and the medical user element can be configured for example wholly or partly as "lock" and "key" (or vice versa) in terms of their external form, in order to enable an unambiguous assignment coupling which preferably cannot be brought about inadvertently.

The depression can comprise a pocket, an insertion slot, a bulge, a groove or combinations of the aforementioned and/or other depressions. In some embodiments, the depression, in terms of its external shape, visually for the user, can be unambiguously assigned to the shape of the medical user element, such that a user intuitively recognizes that the medical user element has to be completely or partly inserted into said depression in order to bring about the assignment coupling and thus to initiate the automatic assignment step automatically without performing further actions. In this way, incorrect operations can be further reduced or preferably completely avoided.

In this way or in some other way, it is possible to realize the "Pairing By Near Closing" already described above, which brings about the temporary predefined coupling alignment. In this way, the control device and the medical user element can be prepared for an authentication process during the assignment step.

A further possibility—which can likewise be used alternatively or additionally—for the configuration of the medical system or the assignment coupling has already been discussed above. In this case, the assignment coupling comprises an exchange of biometric features. Accordingly, the control device and the medical user element in each case can have, for the purpose of the assignment coupling, for example, an interface in the form of one or more detection devices for detecting one or more biometric features of the user. As an alternative or in addition to the actual user, in particular it is possible in this case, too, for a third person also to provide the biometric features in order to obtain the assignment, for example a physician, a pharmacist, a caregiver, a spouse or a medical technician who sets up the medical system for the user.

In this case, biometric features should generally be understood to mean unambiguous biometric information which can serve as assignment identification. Examples of such biometric features are a shape of an iris of the user, fingerprints or the like. For this purpose, the detection device can comprise, for example, a fingerprint scanner, an iris scanner or similar detection devices, such that the same biometric feature can be detected firstly by the medical user element and secondly by the control device in order to assign them unambiguously to one another. The assignment coupling can then comprise a handling of the medical user element and of the control device by the user (or analogously a third person), which can take place simultaneously or successively, wherein the medical system is designed to initiate the assignment step upon recognition of the same biometric feature by the detection device. The detected biometric feature therefore serves as assignment identification within the meaning of the above description or at least as part of said assignment identification. The handling by the user is effected for example by means of a body part, for example a hand, wherein the biometric features can be detected, in particular a fingerprint of the hand. In this case, the detection devices can preferably be configured in such a way that the biometric feature is not detected during normal operation, for example normal medical operation, for example by means of a corresponding covering and/or an arrangement at locations which usually do not come into contact with the relevant body part.

The medical system can be designed, in particular, to automatically start medical operation wholly or in part upon or after successful completion of the assignment step. For example, measurement operation of a sensor can be started automatically. Further handling by a user is not necessary in this case; rather, a genuine plug-and-play system arises which can automatically commence its operation after the assignment step and can exchange personal data, for example.

The medical system can comprise one or a plurality of medical user elements. If a plurality of medical user elements are provided, then the control device and the medical user elements can form a medical network. This medical network can furthermore comprise further components, which do not come under the term medical user element or under the term control device, such as, for example, devices which have no medical function. Thus, an interface device and/or a storage device can be provided in order to exchange data between the medical network and other components, for example with other networks. In principle, the number of components to be assigned and/or the temporal assignment and order are not limited or prescribed. Thus, a data logger module can optionally be provided, for example for purposes of evaluating the personal data and/or other data.

Alternatively or additionally, the user can evaluate personal data collected by the medical user element, for example a sensor, directly in a PC system with a physician by said data being loaded onto the PC system (upload). This process can also require pairing, for example with performance of an assignment step in accordance with the above description. The medical system can furthermore be designed to enable an automatic inclusion of further medical user elements by means of further automatic assignment steps within the meaning of the description above. In this way, the medical network can be extended according to the plug-and-play principle, but it can always be ensured that personal data are exchanged only between elements assigned to one another, for example a specific control device and a specific medical user element.

As described above, the control device can comprise at least one user interface for exchanging data and/or commands with the user, in particular an indicator element and/or an operating element. The medical user element typically does not comprise such elements which enable the user to directly access functions and/or data of the medical operating element, such that the medical user element can be configured for example wholly or partly as a cost-effective disposable element fashioned in a simple manner. In particular, the medical user element can also be configured without operating elements and/or indicator elements, such that the medical system can be operated for example completely via the control device. The control device can comprise at least one data processing device, for example a microcomputer. The data processing device can be designed to process the personal data at least in part. Processing in this sense should generally be understood to mean storage of the data, representation of the data for a user, indication of trends or other measurement results, and at least partial analysis of the data (for example by filtering, evaluation or the like) or database functions or combinations of the aforementioned or other processing functions. Alternatively or additionally, the user element can also comprise at least one data processing device, for example a microcomputer and/or a microcontroller.

The control device can be configured, as described above, as a portable control device and can comprise a mobile communication device, such as a mobile radio device. Portable computers can also be encompassed, for example PDAs (Personal Digital Assistant). In some embodiments, the control device itself has at least one measurement function independent of the medical user element. In this case, an independent measurement function should be understood to mean a measurement function, that is to say the detection of a physical and/or chemical and/or physiological property of the user, which is effected independently of a measurement carried out by the medical user element. Although this can involve a measurement variable which is likewise detected by the medical user element, said measurement variable is detected independently by the medical control device. In particular, this measurement function can be a measurement function for detecting at least one property of the body of the user, for example a bodily function and/or an analyte concentration. The control device can be a control device which is designed to qualitatively and/or quantitatively detect an analyte in a body fluid by mean of least one test element, for example a test strip and/or a test tape and/or a test dial. The medical system can be designed, in particular, to carry out a calibration measurement by means of the measurement function of the control device, for example a calibration measurement on blood glucose. In particular, the control device can be designed to detect an analyte qualitatively or quantitatively in a blood sample, in particular a whole-blood sample. Thus, the control device can simultaneously be a measuring device for glucose from whole-blood. These measurement values can be used for example as a reference measurement method. In this way it is possible for example to evaluate measurement signals which can be contained in the personal data, for example, wherein calibration information obtained by the control device is used during the evaluation.

The medical user element can be configured in various ways and comprise various medical functions. Thus, the medical user element can comprise a sensor for detecting at least one analyte in a body fluid, in particular a sensor that can be implanted into a body tissue. By way of example, the sensor can be used in a continuous monitoring glucose system. The sensor can comprise, for example, as explained above, one or more disposables, one or more re-usables, read-out and data management components.

Alternatively or additionally, the medical user element can furthermore comprise a measuring device for detecting at least one bodily function. Said measuring device can comprise one or more of the abovementioned sensors for qualitatively and/or quantitatively detecting the analyte in the body fluid. However, other bodily functions can also be detected, in principle, such as, for example, body temperature, blood pressure or the like. Once again alternatively or additionally, the medical user element can also comprise a medication device, that is to say a device which is able to deliver specific substances such as medicaments to the body. Insulin pumps, in particular, can be mentioned here as an example. Once again alternatively or additionally, the medical user element can also comprise one or more medical actuator devices comprising at least one actuator for controlling a bodily function. Pacemakers, valves or the like can be mentioned here as examples.

In the case of implantable sensors, the assignment coupling can implemented in a non-implanted state. Alternatively, however, the assignment coupling can for example also be designed in such a way that it is effected with a non-implanted part of the otherwise implanted sensor. The above-described embodiments in which the medical user element does not have its own actuator system for directly signaling states to the user and no input/output interface can be desired for use with implantable sensors. Generally, it should be pointed out that the medical user element can also comprise for example a plurality of functions, for example a plurality of measurement functions or combined measurement functions and actuator functions.

The medical system can furthermore be designed in such a way that information about one or more current and/or previous assignments is stored in the control device and/or the medical user element. By way of example, a pairing, that is to say an assignment, and/or an instantaneous secure wireless communication connection can be represented unambiguously on the control device. In this embodiment, the user can rely on the fact that data or, in the case of an emergency also alarms can be transmitted securely. In this case, a pairing, an assignment and/or a secure communication connection can be represented. In addition, a setting-up with the aim of security can also be effected in such a way as to make it recognizable to a user whether or not a communication connection currently exists and/or whether said communication connection is configured securely. For this purpose, it is possible to provide, for example, one or more indicator elements of optical and/or acoustic and/or haptic and/or other type. One or more symbols can be provided which enable a visual indication. Thus, the user can see with the aid of a red or green luminous or flashing radio tower symbol or other symbol or hear by means of an acoustic indication (e.g. by virtue of different tones) whether a communication connection currently exists securely (e.g. green illumination) or does not (e.g. red illumination). It is also possible to make it recognizable whether or not the user can rely on the fact that a spontaneous alarm, for example on account of hypoglycemia, is actually transmitted spontaneously. In this case, spontaneously can be understood to mean a near-instantaneous sequence, for example within a time period of less than one minute. This can prevent the user from mistakenly relying on such alarms being transmitted when in actual fact the connection, for example a radio connection, is not currently provided, for example on account of disturbances, range problems or other technical problems, and/or an alarm does not get through.

The medical system can furthermore be designed to enable an automatic separating step. This automatic separating step can prevent a further exchange of personal data between the medical user element and the control device. This can mean, in particular, that the assignment between the medical user element and the control device is canceled or un-paired.

In this case, the separating step should be effected in a defined manner and initiated only under defined conditions as far as possible in just the same way as the assignment step. Thus, an un-pairing should not be initiated or confirmed merely by the actuation of a key or some other simple actuating element, but rather in just as unambiguous a manner as the pairing. In this way it is possible to prevent a situation in which, as a result of careless actuation of an actuating element, the assignment and hence the connection, for example, is interrupted and problems, for example, can thus occur with regard to transmission of data in the case of an emergency or transmission of alarms. In particular, the un-pairing can be initiated by a user action which deviates considerably from an actuation of the medical system in normal operation.

The separating step can be initiated by the above-described assignment coupling being brought about anew, for example in accordance with one or more of the embodiments described above. In this respect, reference can once again be made to the above description. The system can be designed such that when the assignment coupling is brought about anew, the assignment step is carried out anew and in this case is interpreted as a separating step. Accordingly, reference can largely be made to the above description of possible options. By way of example, a first instance of bringing about the assignment coupling can be interpreted as initiation of a pairing and a second instance of bringing about the assignment coupling can be interpreted as initiation of the un-pairing, wherein, if appropriate, further instances of bringing about assignment couplings can be interpreted alternately as initiation of pairing and un-pairing. The system can furthermore be designed so that in each case the current state between a specific medical user element and the control device is made recognizable for the user, for example via an indicator element. Thus, by way of example, on a display of the control device, it is possible to indicate whether, with one or more medical user elements situated in a range for a data exchange, there is pairing or un-pairing, that is to say whether or not an exchange of personal data can take place. Alternatively, an automatic separating step can also be initiated by some other process, for example by pressing a key or the like.

The medical system can furthermore also comprise a failsafe concept, that is to say a concept which converts the medical system or one or more components of the medical system to a safe state in an unexpected situation, for example an occurrence of a fault. By way of example, the medical user element and/or the control device, optionally also without the possibility of audible or visual notification of the user, can comprise one or more algorithms for being brought to a safe state when a fault occurs. By way of example, the medical user element can be designed to establish the safe state when a fatal fault occurs, and, for example, upon the next opportunity, to communicate the occurrence of the fault, the safe state or other information to the control device. Various other configurations of a failsafe concept in the context of the plug-and-play concept proposed are conceivable.

Further possible configurations of the medical system concern the exchange of data, for example the personal data or data which can comprise the medical data. Thus, the freedom of movement of the user is intended to be restricted as little as possible by the data exchange, which, as described above, takes place wirelessly. Accordingly, the data exchange should take place so rapidly that all the data to be transmitted are transmitted within the time within which the user moves past a control device in the course of normal movements, which can also be described as data transfer "by the way". Typical movement speeds of users are approximately 1 m/s. Accordingly, the control device can be accommodated in a stationary fashion and separately from the user, whereas the medical user element is connected to the user and moves along with the latter. The connection set-up and the useful data transmission should accordingly be effected within this time, thus resulting in typical data transmission rates of more than 100 kbit/s.

Since radio systems usually operate in physically undefined environments, transmission links are disturbed in many cases. This can have the effect that a transmission upon establishment of proximity under unfavorable circumstances does not take place completely or else is totally disturbed. In order to reduce this risk, in the medical system proposed it is possible to transmit a temporal profile of personal data, for example measurement values, in compartments. It is proposed that the medical system is designed to enable a repeated exchange of complementary data records at least upon repeated momentary establishment of proximity between the control device and the medical user element in medical operation. By way of example, curve progressions, that is to say a plurality of data points, can be transmitted, in which case a subset of the data records is respectively transmitted during each transmission process. Said subset can cover the entire region of the curve progression and/or of a time interval under consideration, but with comparatively low temporal and/or dynamic resolution. By way of example, it is possible to transmit individual data records which were recorded at equidistant temporal separations. It is thus possible that although the curve progression is not represented with complete accuracy, it is nevertheless represented qualitatively well and completely, even if only one or a few transmission processes take place. Upon the next establishment of proximity, if appropriate, a further but different subset of the data to be transmitted can then be transmitted, followed if appropriate by further transmission processes. Thus, a first, relatively short data packet already allows the representation and/or evaluation of a complete curve of the data points detected until then, which becomes more accurate with each data record, up to complete transmission of the data record.

As explained above, alongside the medical system, a method for operating a medical system, in particular a medical system in accordance with one or more of the embodiments described above, is furthermore proposed. In this case, a control device and at least one medical user element are used. The medical user element and the control device are designed to exchange data wirelessly. In the method, an automatic assignment step is carried out, wherein an exchange of personal data between the medical user element and the control device is enabled by the automatic assignment step. The automatic assignment step is automatically initiated by means of an assignment coupling between the medical user element and the control device. The assignment coupling is subsequently separated again for medical operation of the medical system. For further possible configurations of the method, reference can be made to the above description.

The medical system and method proposed have numerous advantages over known systems and methods. Thus, the above mentioned disadvantages of known systems, for example of continuously measuring self-monitoring diabetes systems, can be largely avoided by means of the medical system proposed, for example by means of consistent plug-and-play conceptions. In this case, the plug-and-play concept can relate to the entire interactive action sequence between the medical system and the user.

The user can be enabled, in particular, just with elementary action steps, such as, for example, unpacking from a primary packaging, preparing the biological application, attaching the system to the body and carrying out an implantation, to start a subcutaneous continuous glucose measuring process and to keep it in operation. At the end of a measurement cycle, a removal of the system or of the medical user element can then be carried out manually. Generally, upon or after the removal of the medical user element, for example the separating step described above, if appropriate, a data protection step can automatically be instigated, in the course of which, for example, measurement data can be transmitted from the user element to the control device and, if appropriate, stored there.

The medical system can furthermore be embodied in such a way that insertion of subcomponents, for example data carriers, batteries or the like, and/or data inputting and/or activation and initialization of sequences by the user can largely be obviated. The medical system and the components thereof can be embodied for example in such a way that they only have to be configured minimally by the user, for example only by settings of country languages and time zones. However, these steps, too, could optionally be performed automatically by the medical system or individual components of the medical system, for example by the establishment of spatial coordinates by means of GPS localization and/or by means of radio time systems. The reference to an exact time may, if appropriate, be therapeutically important, for example in the case of diabetes with regard to the administration of active substances. Precisely when journeys are made, therefore, an automatic changeover of the time, for example a local time in relation to an absolute time, can be important. The medical system can be designed to perform such an automatic changeover. By way of example, a function of the medical system, in particular a function of the medical user element, can be completely or partly adapted to a local time, for example automatically. By way of example, a controlled delivery of medicaments or some other medical function can be adapted to a local time, in particular automatically, such that, by way of example, jetlag is not accompanied by therapy-lag.

By means of the medical system, for example in the case of self-monitoring diabetes systems, measurement values and results can be assigned to a defined user unambiguously and in the manner free of errors. This is becoming increasingly important since systems of this type nowadays are spatially distributed to an increased extent and are accordingly made available to the public to an increased extent, for example in the context of medical offices, communication media or the like.

Moreover, the medical system affords the advantage that not only can system components and entire medical systems be started up and deactivated in a simple manner, but that accordingly unambiguous assignments of two or more system components to one another can also be effected in a simple manner by means of simple action sequences. Besides the unambiguity of the assignment, it can also be noted as advantageous that the user is not restricted, or is restricted only to an insignificant extent, by the proposed medical system in terms of said user's freedom of action and freedom of movement.

BRIEF DESCRIPTION OF THE DRAWINGS

Further details and features of embodiments of the invention will become apparent from the following description of certain exemplary embodiments. In this case, the respective features can be realized by themselves or as a plurality in combination with one another. The invention is not restricted to the exemplary embodiments. The exemplary embodiments are illustrated schematically in the figures. In this case, identical reference numerals in the individual figures designate elements that are identical or functionally identical or correspond to one another with regard to their functions.

DETAILED DESCRIPTION

Figure 1:
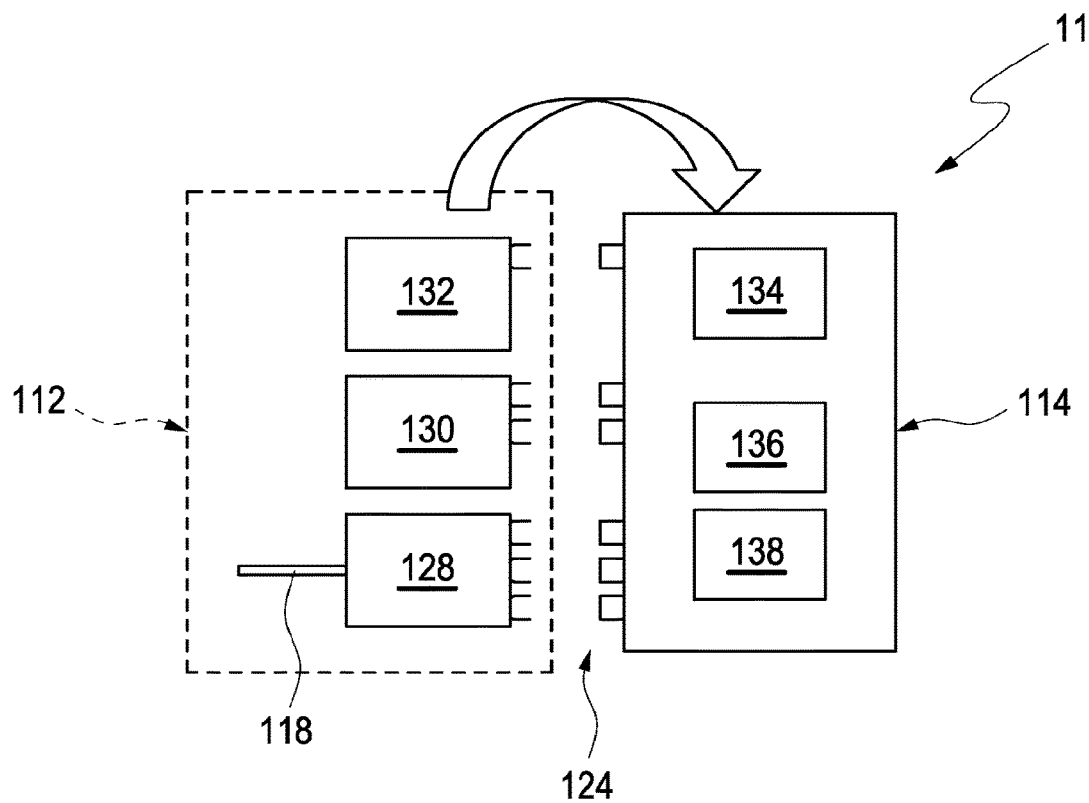
FIG. 1 shows an example of a medical user element in the form of an implantable sensor.

A medical system embodiment according to the invention is described below by way of example of a continuous monitoring glucose system. A system of this type comprises a sensor 110, which is illustrated symbolically in FIGS. 1 and 2 and which has a disposable unit 112 and a reusable unit 114. These units 112, 114 are illustrated schematically in FIG. 1. FIG. 2 illustrates a process of implantation of the sensor 110 by means of an implantation aid 116, which, if appropriate, can be removed again later.

The sensor 110 comprises a sensor 118 that can be inserted into the body tissue, for example interstitial tissue. In this case, the disposable unit 112 and the reusable unit 114 are not illustrated in FIG. 2. By way of example, after the sensor element 118 has been implanted into the body tissue 120 of a user 122, the reusable unit 114 can be connected to the disposable unit 112 via an interface 124 (see FIG. 1), in particular a pluggable hardware interface. The sensor 110 can furthermore comprise a sensor plaster 126, by means of which the sensor 110 can be stuck on a skin surface of the user 122.

Figure 2:
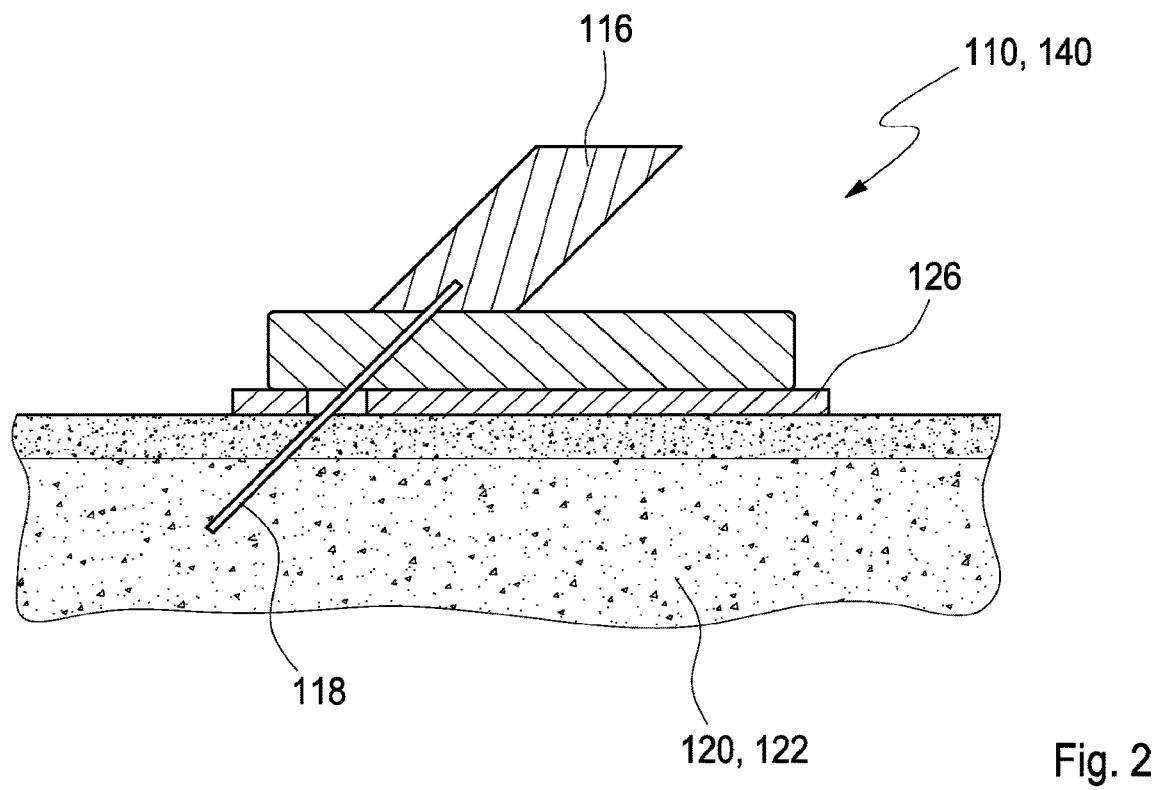
FIG. 2 shows the implantable sensor during implantation in a sectional illustration from the side.

As emerges from the schematic illustration in FIG. 1, the sensor 110, for example the disposable unit 112, can comprise, for example alongside a sensor unit 128 for recording measurement data, an energy store 130 and, if appropriate, a data memory 132 for the buffer-storage of sensor data. The reusable unit 114 preferably does not have its own energy store and is supplied with electrical energy by the disposable unit 112. The reusable unit 114 can likewise comprise a data memory 134 and also an interface 136 for wireless data exchange with a control device, with for example a radio interface. Furthermore, an interface 138 can be provided, which can be completely or partly different than the interface 136 and for which can be used for the automatic assignment step described below, which is also designated below as pairing. Via said interface 138 the assignment coupling described above can be effected, by means of which the assignment identification can be exchanged.

The sensor 110 illustrated in FIGS. 1 and 2 forms a medical user element 140, which is assigned to a user 122 and can be carried continuously by said user, in particular directly on or in the body. As an elementary step of handling the sensor 110, in the present example, the disposable 112 is unpacked, said disposable 112 is connected to the reusable 114 and the sensor element 118 is inserted into the body tissue 120. The functional unit thus produced is therefore ready for operation and can begin detecting measurement values automatically. The described unit of the sensor 110 then can operate autonomously providing information such as personal data, in particular measurement data, times, results or the like, but outwardly not visible. In order to further process and represent these measurement values, therefore, a control device 142 is required (see FIG. 3, for example). At least one control device 142 of this type and the at least one medical user element 140 together form a medical system 144. The control device 142 can comprise for example a measuring device, for example a blood glucose measuring device. Alternatively or additionally, it can also comprise a data manager and/or further-processing computer systems.

The data exchange from the sensor 110, which in this case serves as a measurement value detection module, toward the control device 142, in this case the blood glucose measuring device, has to be configured in such a way that this can be assigned unambiguously. A situation in which data from a neighboring system reach a non-authenticated memory and/ or an incorrect indicator unit should be avoided at all events. In order that components are authorized for exchanging private data, before the beginning of the operation of the medical system 144, a deliberate authentication step should be carried out in the context of an automatic assignment step, which is also designated as pairing. In this step, by way of example, one or more device numbers, in particular unique device numbers, for example of the control device 142 and/or of the sensor 110, can be exchanged. These device numbers and/or other types of assignment identifications can be stored for example in one or more data memories in the control device 142 and/or the sensor 110, and, if appropriate, linkages can be produced. By way of example, a unique device number of the sensor 110 can be stored in the data memory 132, which number, if appropriate, can be exchanged and used to establish a linkage in the control device 142, for example, such that after the automatic assignment step has been carried out, for example, the control device 142 knows that personal data can be exchanged with this specific sensor 110. Although the automatic assignment step is intended to be carried out in a very deliberate manner by the user 122, it is nevertheless intended not to have the potential for error of manual number or code inputting.

In conventional point-to-point plug connections this can easily be ensured since the user 122 in this case actively and consciously produces the plug connection and, given correct construction, no signals can be fed in or tapped off externally. This is not ensured, however, in the case of optical connections and primarily in the case of radio connections. However, cableless connections and specifically radio connections nevertheless have numerous advantages with regard to flexibility and modularity of product concepts. In the case of the sensor 110 proposed, therefore, the abovementioned interface 136 is designed for wireless data exchange, in particular as a radio interface.

FIGS. 3 to 6 illustrate different examples of embodiments of medical systems 144 according to the invention and embodiments of automatic assignment steps. In each of these cases, an assignment coupling between the control device 142 and the medical user element 140 that is to be coupled thereto is produced, by means of which at least one assignment identification can be exchanged between the control device 142 and the medical user element 140.

Figure 3:
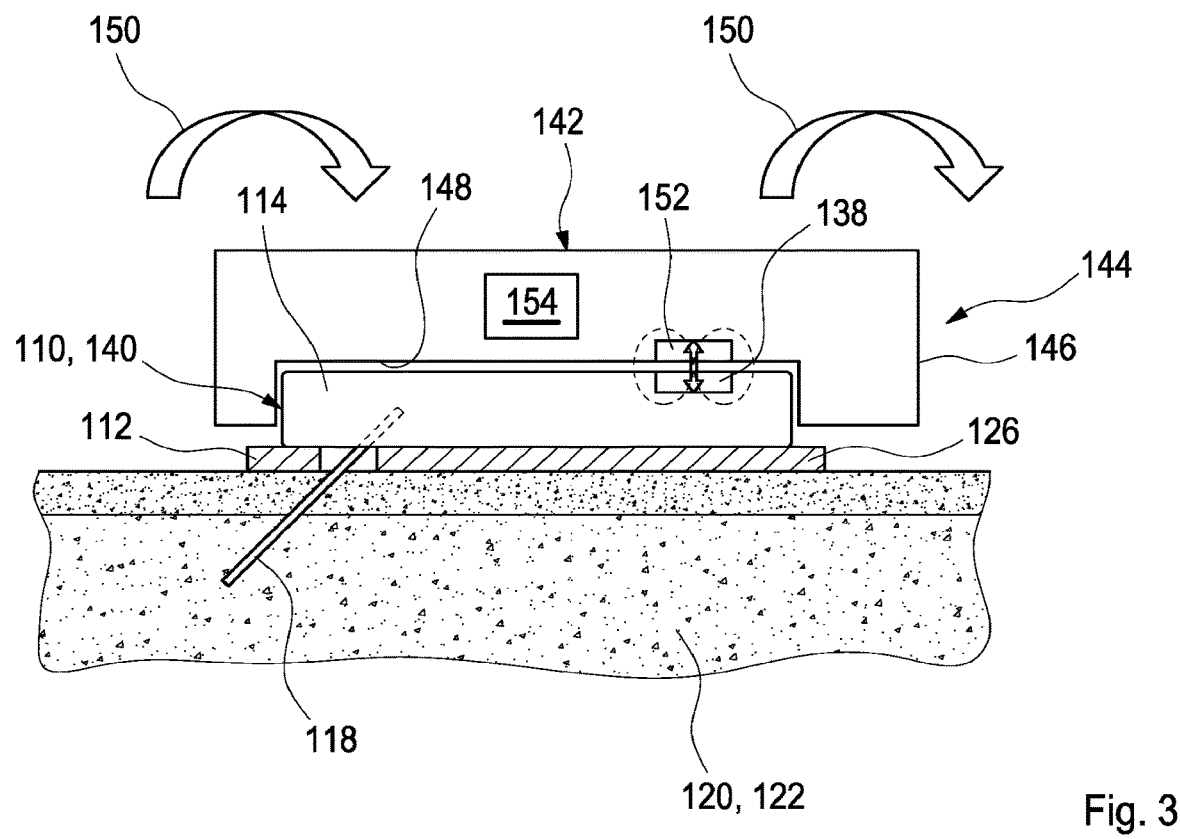
FIG. 3 shows a first exemplary embodiment of "pairing by near closing."
Figure 4:
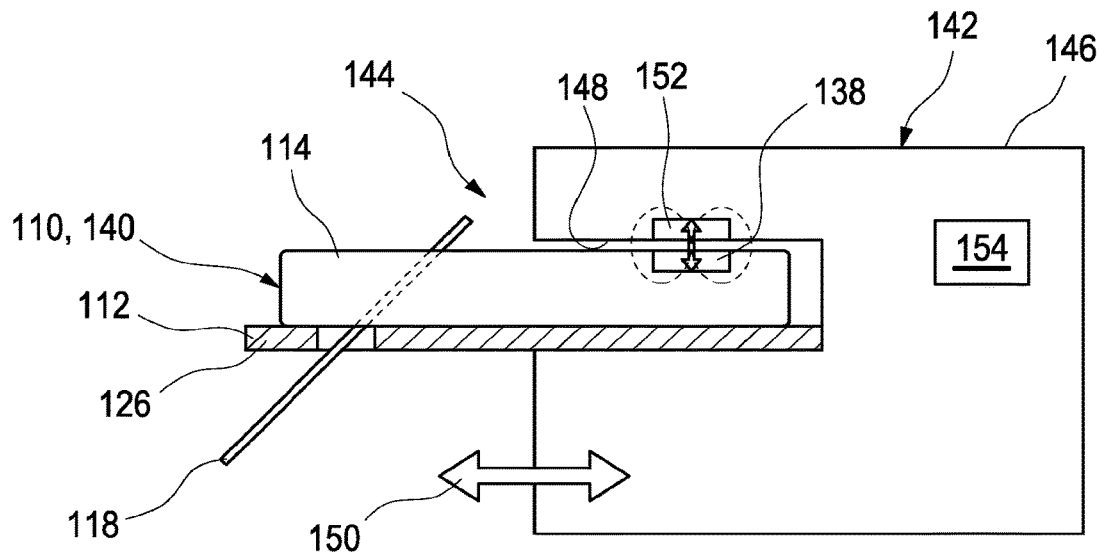
FIG. 4 shows a second exemplary embodiment of "pairing by near closing."

Thus, FIGS. 3 and 4 show different exemplary embodiments of a medical system 144, in which the medical user element 140 and the control device 142 are designed in terms of their external shape in such a way that they can be brought into a defined temporary coupling alignment relative to one another, in which the abovementioned assignment coupling is present and hence the assignment step is initiated, in which, in turn, the at least one assignment identification can be exchanged. In both cases, the control device 142 can for example again be configured as a blood glucose measuring device. The control device 142 has a housing 146, which has a depression 148 adapted to the external shape of the sensor 110. Said depression 148 enables a positively locking connection between the sensor 110 and the control device 142, which connection can be brought about deliberately and temporarily by the user 122 in order to produce the assignment coupling and thus to initiate the assignment step described above. In this case, the exemplary embodiments in FIGS. 3 and 4 differ to the effect that in FIG. 3 the sensor 110 has already been implanted in the body tissue 120 of the user 122, and that the control device 142 can only be placed from above onto the externally accessible part of the sensors 110, for example only onto the reusable unit 114. The latter can have for example a square or rectangular plan, to which the plan of the depression 148 can correspond, such that the user can bring about an assignment orientation without major difficulties. In the exemplary embodiment in accordance with FIG. 4, by contrast, the depression 148 is configured as a pocket, into which the sensor 110 can be inserted by its narrow side.

In both cases, the assignment step is initiated by the assignment coupling illustrated in FIGS. 3 and 4 with the assignment orientation illustrated. In both cases, the assignment step or the initiation thereof by the production of the assignment coupling is designated symbolically by the reference numeral 150. Before the assignment step 150 is carried out, the medical user element 140 and the control device 142 are in a non-assigned state ("unpaired"), whereas after the assignment step 150 the two elements 140, 142 are in an assigned state ("paired").

As explained above, the medical user element 140, for example the sensor 110, has, a separate interface 138 for the assignment step. This separate interface 138 can be designed as an interface that does not involve direct electrical coupling for a data exchange that does not involve direct electrical coupling. In an analogous manner, the control device 142 can have an interface 152, which is designed specifically for the assignment step and which is preferably embodied separately from an optional further interface 154 for the wireless data exchange, for example a radio interface. In the coupling orientation illustrated, the interfaces 138, 152 can in each case be oriented with respect to one another in such a way that they can exchange the assignment identification. The assignment step can be initiated and carried out in this way.

Figure 5:
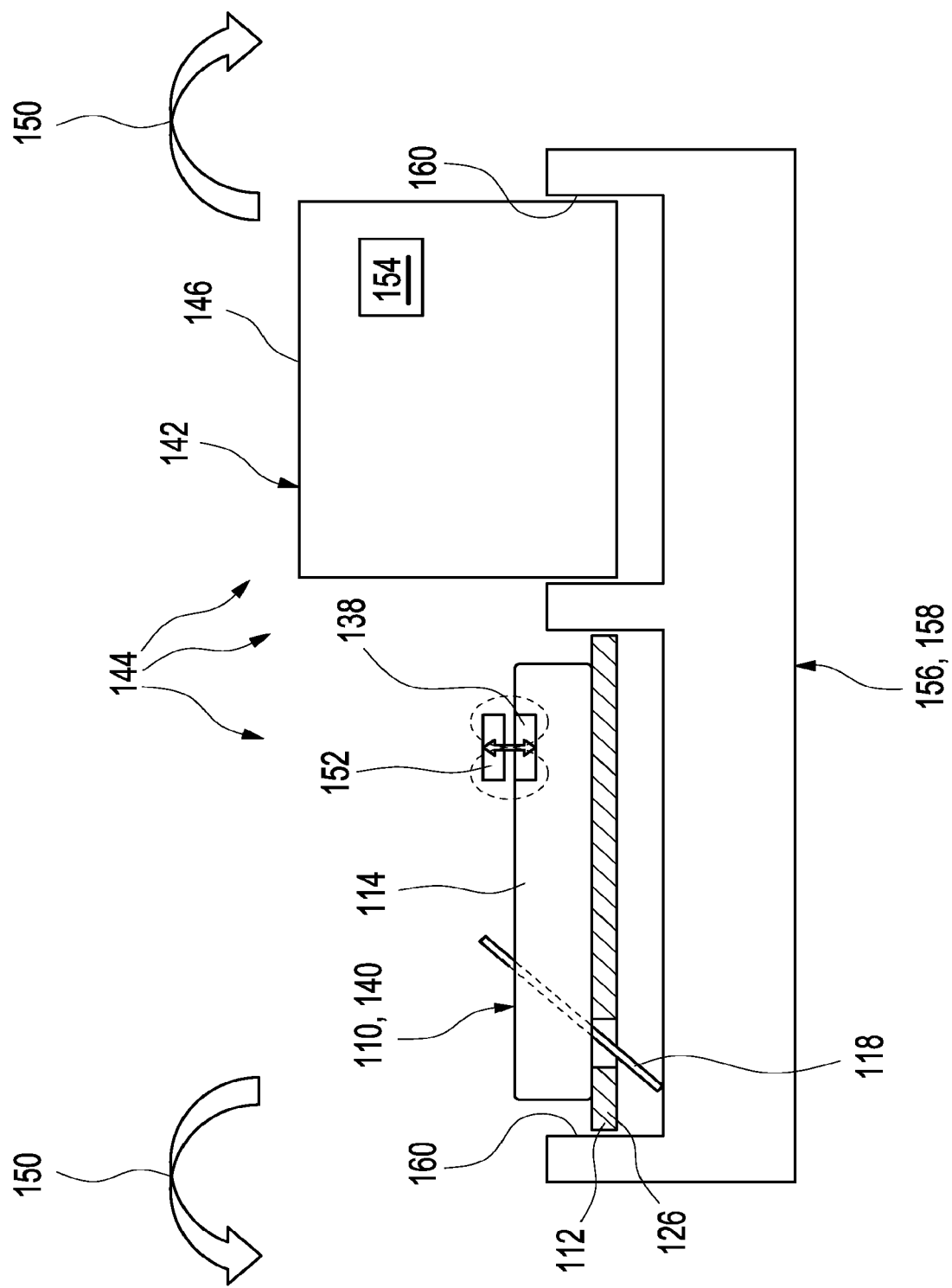
FIG. 5 shows an exemplary embodiment of pairing by using a docking station.

FIG. 5 illustrates a further exemplary embodiment of the medical system 144, in which the assignment coupling is effected by means of a coupling element 156 in the form of a docking station 158. In this case, the docking station 158 has one or two interfaces 160, to which the medical user element 140 and the control device 142 can be mechanically and/or electrically connected successively or simultaneously. By means of said interfaces 160, a purely mechanical orientation of the control device 142 and of the medical user element 140 with respect to one another can be effected, for example for an optimized exchange of the assignment identification. In FIG. 5, in this case the interface 152 of the control device 142 is merely indicated symbolically. The assignment identification can be exchanged directly from the interface 138 to the interface 152, as indicated in FIG. 5, or for example via a third interface, which can be part of the docking station 158 and which can also be embodied in multipartite fashion. In this way, the assignment information can be exchanged by means of the docking station 158 as coupling element 156.

Figure 6:
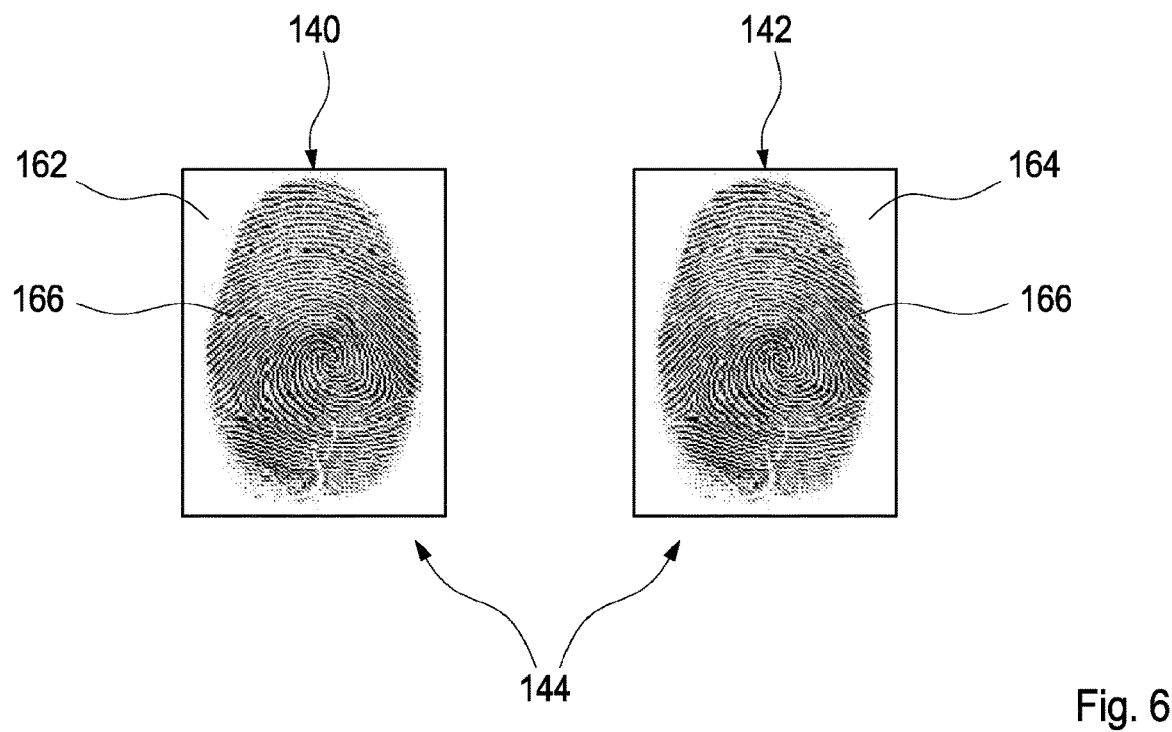
FIG. 6 shows pairing by recording biometric features.

A third possibility for the assignment coupling between the medical user element 140 and the control device 142 is illustrated symbolically in FIG. 6. In this case, both the medical user element 140 and the control device 142 each have a detection device 162 and 164, respectively, for detecting a biometric feature of the user. In this case, the biometric feature is symbolically designated by the reference numeral 166 in FIG. 6 and can comprise a fingerprint, for example. The detection device 162, 164 can accordingly comprise a fingerprint scanner, for example in the form of a scanner array and a scanner line. Other biometric features 166 can also be used. The assignment step is initiated by the user successively applying the latter's fingerprint or the other biometric feature 166 onto the detection device 162 and 164. If the biometric features 166 match, then they function as assignment information and bring about an automatic pairing between the control device 142 and the medical user element 140. If the medical system 144 has detection devices 162, 164 of this type, then it is possible, if appropriate, to dispense with separate interfaces 138, 152 for the assignment step since the detection devices 162, 164 in this case themselves act as interfaces of this type. The biometric features can for example be converted into data, for example binary data, and, if appropriate, can be encrypted and/or stored, in particular as codes, in the individual modules, for example in the medical user element 140 and/or in the control device 142. Upon contact, the codes can be compared and, optionally, personal data can then be exchanged in the event of identity. In this way, a permanently required pairing can be obviated and, if appropriate, also an un-pairing, since a pairing can be carried out automatically for example upon every new communication set-up by means of a code comparison.

The possible configurations illustrated in FIGS. 3-6 constitute only a selection of possibilities for how an assignment step can be initiated by means of the assignment coupling. Thus, in FIGS. 3 and 4, for example, the combination of an unambiguous and deliberate manual action on the part of the user 122 is achieved by means of so-called "near closing". For this purpose, the user 122 can bring for example the sensor 110, for example a patch-type sensor 110, so near to the control device 142, for example the blood glucose measuring device, that an unintentional physical contact with an unauthorized module is virtually impossible. As indicated in FIGS. 3 and 4, this can for example also be effected by means of momentary, at least partial insertion of the medical user element 140 into the depression 148, for example a housing pocket on the blood glucose measuring device. Some other geometrical configuration of the user element 140 and/or of the control device 142 for preventing an unintentional assignment coupling is also possible, in principle. Thus, an unintentional assignment coupling can generally be prevented by mechanical forms of the control device 142 and/or of the user element 140, for example lock-key forms.

After the assignment step has been carried out, said assignment coupling can then be canceled again, the two components 140, 142 can be separated again, and normal medical operation can be initiated. In this medical operation, for example personal data and measurement data of the sensor 110, can be exchanged between the medical user element 140 and the control device 142, via the interfaces 136 and 154. Alternatively, as shown with reference to FIG. 5, an assignment can also be effected via the docking station 150, into which the medical user element 140 and the control device 142 can be momentarily introduced, for example placed. If such a positively locking connection arises, then it is possible to exchange data in digital form between the modules 140, 142 to be assigned to one another (that is to say to be paired), in other words for example an assignment identification which carries out, confirms and concludes the pairing process. The two components 140, 142 can then be physically separated again and are henceforth assigned to one another (paired). This assignment can be effected for example until an active "un-pairing step" takes place, that is to say a separating process, for example by means of renewed near closing, for example analogously to one or more of the embodiments in FIGS. 3-6.

Since the sensor 110, for example, can be a high-impedance electrochemical sensor system, data exchange via direct electrical connections is functionally critical in general. Therefore, an electrically hermetic encapsulation of the sensor 110 should generally be striven for. Therefore, one or both of the interfaces 136, 138 are designed for a data exchange by means of electromagnetic fields, in particular the interface 138. However, the interface 136, too, which can also be configured wholly or partly identically to the interface 138 in respect of components, can be configured in this way. The data exchange in a manner not involving direct electrical coupling can be effected, for example, via spatially closely coupled wire coils (that is to say inductively, in particular) and/or via insulated capacitor plates (that is to say capacitively, for example) or by means of RFID. Alternatively or additionally, an optical data exchange (for example via a light barrier) can also be effected, which presupposes a physical visual contact. All of these methods which can be used for the assignment step and which necessitate corresponding setting-up of the interface 138 for the assignment step largely prevent unintentional pairing with components randomly situated in the vicinity.

The medical system 144 can be designed in such a way that, apart from the actions described above, no further actions need be carried out by the user 122. However, further actions of this type can optionally be provided. Thus, for further security of the method, the assignment step can also be initiated or enabled by the use of a further, independent function, such as pressing a key (for example on the control device 142 and/or on the medical user element 140). A further possibility for reducing the probability of incorrect coding or incorrect allocation is a defined temporal code upon establishment of proximity of the two components 140, 142. A unique assignment also allows the linkage described with reference to FIG. 6 by means of biometric features 166, of the user 122, such as fingerprints, iris patterns or the like. However, this configuration generally means a comparatively great outlay on apparatus, which, however, in the context of the increasing prevalence of such safety systems (for example the availability of cost-effective detection devices 162, 164), is both acceptable in terms of volume and economic in suitable orders of magnitude.

Figure 9:
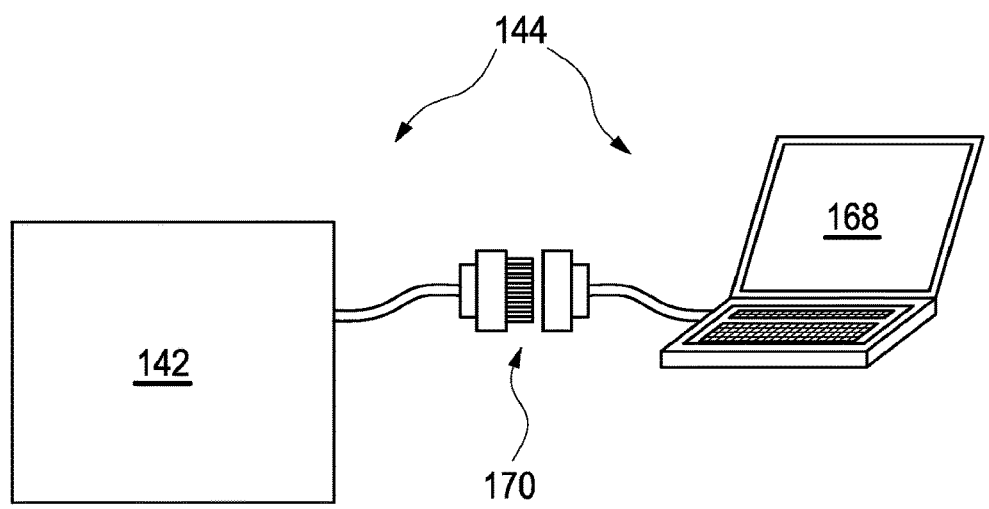
FIG. 9 shows a schematic illustration of a coupling of a computer into a medical system.

The number of components of the medical system 144 that are to be assigned to one another is not limited or prescribed, in principle. Thus, the medical system 144 can also be configured wholly or partly as a medical network and can optionally have for example a data logger module for evaluation purposes. Later, as indicated in FIG. 9, a user can "upload" the personal data that have been collected by said user's sensor 110 or medical user element 140 and have preferably been at least buffer-stored in the control device 142 directly to a computer system, for example a PC system 168, for example a PC system 168 of a physician. This can be effected, for example, as indicated in FIG. 9, via an additional interface 170, which is shown here by way of example as a wire-based interface, for example as an RS232 interface. In this way, the PC system 168 can be incorporated for example into the medical system 144, for example for a short time. This incorporation can for example likewise necessitate a pairing, but can also be effected without an assignment step, particularly when wire-based interfaces 170 are used.

The medical system 144 can also optionally be configured at least in part as an open system and to enable interoperability. Thus, a physician in principle generally cannot adapt to all possible patient-specific or product-specific pairing interfaces, since, for example, a multiplicity of competing products can exist. Accordingly, the medical system 144 can enable for example the incorporation of a specially authorized person or of a specially authorized system component, for example a physician and/or a physician's computer, which can enjoy a special status. Thus, a special mode "physician" can be provided, for example in a radio system. In this special mode, a pairing with the specially authorized person and/or the specially authorized system component could be restricted to software. This could be effected in such a way that a cross-manufacturer convention is adopted which is understood by any medical system 144 and/or the components thereof. In this regard, reference can be made to the above-cited standard IEEE 11073 which can therefore be combined with a medical system 144 according embodiments of the invention.

After pairing has been effected, for example after the steps described with reference to FIGS. 3-6 have been carried out, components of the medical system 144 that can be assigned to one another exchange data automatically as soon as a transmission is physically possible. In the case of typical sensors 110, this can be effected when proximity is established between the two interfaces 136, 154 to more than approximately 1 m. This distance may exist for example through arbitrary layers of clothing. Physically, a transmission is possible, in principle, without spatial alignment and thus through a wide variety of materials practically only by using radio waves. In principle, however, optical data transmissions can also be realized at least to a limited extent in this medical operation.

If two components 140, 142 of a medical system that possibly communicate with one another approach one another, then the medical system 144 can be designed, in particular, in such a way that it automatically checks whether an assignment of these components 140, 142 to one another exists, that is to say whether the latter are authorized for the exchange of personal data, in particular by means of a preceding pairing step. This can be effected for example by means of communication protocols, for example in accordance with the OSI standard. Thus, by means of said communication protocols, for example, a stable contact can be established, and it is possible to check whether an authorization (pairing) is present, and, if this is the case, the specific useful data can then be exchanged uni-directionally or bi-directionally.

Figure 7:
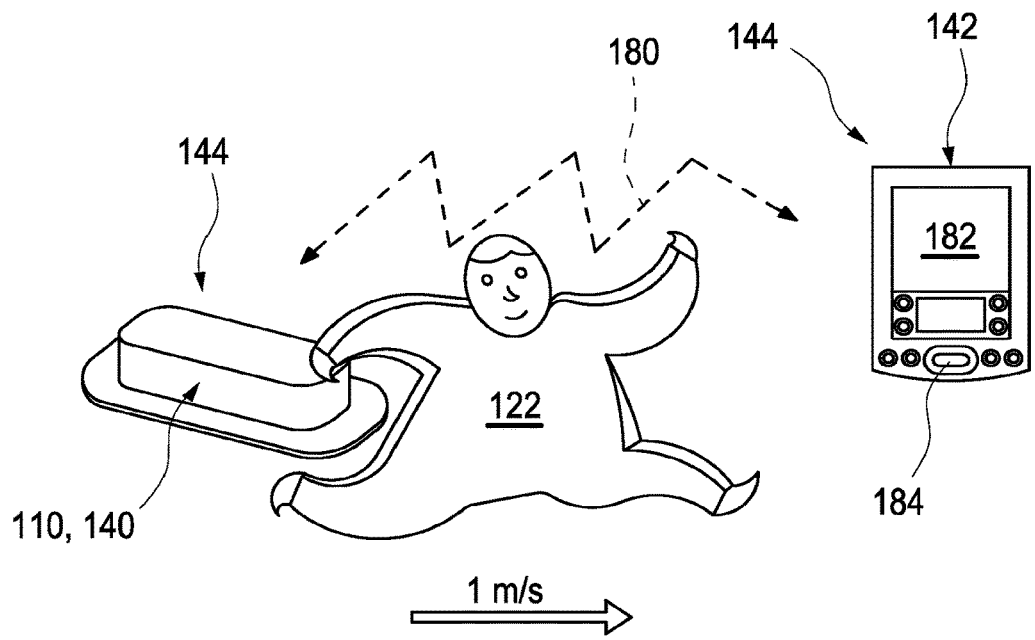
FIG. 7 shows a data transmission from a moving user to a control device that is stationary or moving at a different speed.

In order to comply with minimum restriction of the freedom of movement of the user 122, in medical operation, that is to say after carrying out the pairing step or the assignment step, a data exchange between the components 140, 142 of the medical system 144 that are assigned to one another and should be effected so rapidly that all the data to be transmitted are transmitted within the time within which a user 122 normally moves past a control device not moving together with the user 122. This data transmission can also be designated as "data transfer by the way" and is illustrated symbolically in FIG. 7. By way of example, as indicated in FIG. 7, the user 122 can move at a speed of 1 m/s relative to the control device 142. This means that the connection set-up and the transmission of personal data, such as useful data, for example, should be effected within this time, which should result, as explained above, for example in transmission rates of preferably more than 100 kbit/s. Since radio systems operate in physically undefined environments, however, the transmission links are often disturbed. This has the effect that transmission upon establishment of proximity, under unfavorable circumstances, does not take place completely or else is totally disturbed. In order to reduce this risk, the medical system 144 can be designed, for example, in such a way that the personal data are transmitted by single or repeated exchange of complementary data records. Thus, by way of example, it is possible to transmit temporal profiles of measurement values in compartments. This is illustrated symbolically in FIG. 8, where a set of signals S, for example measurement values, are plotted as a function of a measuring instant t, for example the instants at which the measurement data were recorded by the sensor 110. However, different types of data records than temporal data records are also conceivable, in principle.

Figure 8:
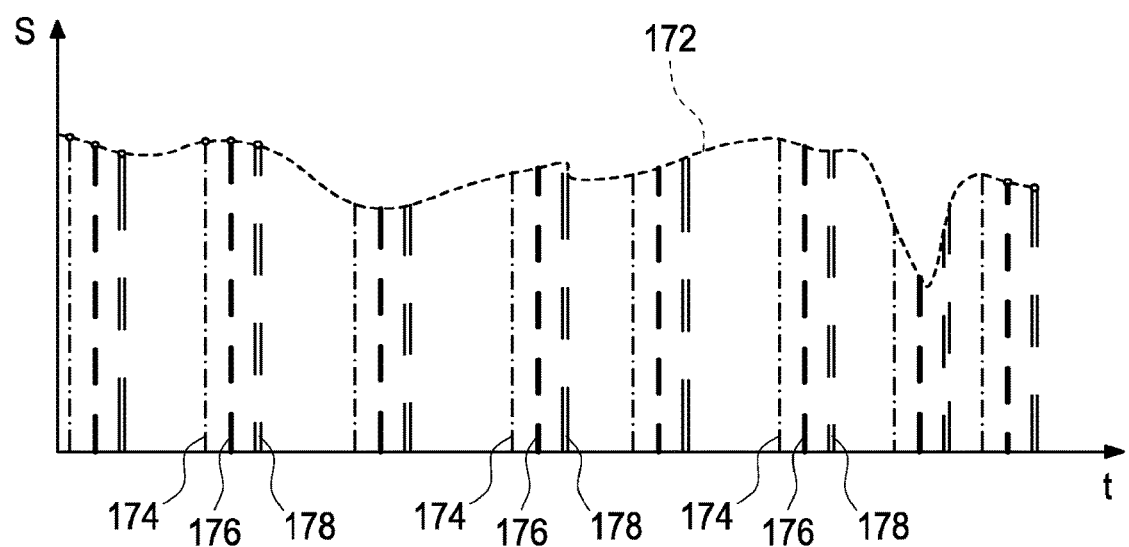
FIG. 8 shows an example of a complementary data transmission.

A curve progression 172 connects all the discrete data records in FIG. 8 and thus maps the temporal profile of the detected signal as a function of time t (i.e. S=f(t)) over a total observation period T. The observation period T is divided into N time intervals, for example equidistant time intervals. The data records in these time intervals are designated by the reference numerals 174, 176 and 178, for example, at the respectively repeating positions in the intervals in FIG. 8.

In this case, a data record can be understood to mean a set of alphanumeric characters enclosed by a so-called frame (start and/or end definition). By way of example, the partial data records designated by the reference numerals 174, 176 and 178 in FIG. 8 can in each case comprise a binary voltage value (S), the associated time (t) and optionally further elements, for example one or more safeguard features such as a CRC character. By contrast, a curve progression 172 can be understood to mean a connection of all the positions (S/t) described in the data records or partial data records in a coordinate system, which is ultimately tantamount to a closed representation of the function S=f(t).

By way of example, the medical system 144 can be designed in such a way that it firstly communicates the first partial data record 174 of the intervals 1 to N wirelessly upon establishment of proximity between user 122 and control device 142. The wireless data exchange is designated symbolically by the reference numeral 180 in FIG. 7. If time then still remains during the establishment of proximity, further partial data records 176, 178 of the intervals 1 to N can be transmitted. Alternatively, however, these can also be communicated to the control device 142 at later instants upon later instances of establishment of proximity.

In this way, it is possible that although the curve progression is firstly not represented with complete accuracy, it is nevertheless represented qualitatively well and completely by the first partial data record 174, which may, if appropriate, be therapeutically more important (e.g. in the event of hypoglycemia) than a high temporal and/or dynamic resolution. If time then still remains or in the context of a next establishment of proximity, further, different partial data records 176, 178 can then be communicated. Thus, a first, relatively short data packet in the form of a partial data record 174 already enables a representation of a well-approximated measurement curve of the curve progression 172, for example on an indicator element 182 of the control device 142. With each communication of a partial data record 174, 176, 178 the representation then becomes more accurate, up to the complete transmission of the curve progression 172. Between a first establishment of proximity at an instant $t_1$ and a further establishment of proximity at an instant $t_n$, in principle an arbitrary amount of time can elapse, such that the data record detection has progressed and the number of intervals has increased to N+M. The intervals N+1 to M can be filled upon a second establishment of proximity, for example, firstly with the partial data records 174 or directly with the partial data records 176, in the same way as the intervals less than N. Alternatively, however, other strategies for the data organization of a continuous data acquisition are also possible.

The control device 142 is illustrated symbolically as a PDA in FIG. 7, with the indicator element 182 in the form of a display and one or more operating elements 184. Alternatively or additionally, however, the control device 142 can also be configured as a blood glucose measuring device, for example, as has already been described above. Thus, the control device 142 can be configured for example as a measuring device for glucose from whole blood. The measurement values of said measuring device can be used for example as a reference measurement method, for example in order to calibrate the medical system 144. The whole-blood measuring device may require, for example, similarly to the sensor 110, a data carrier that conveys batch-specific data from test elements to the measuring device. This can be effected by the manual insertion of an electronic data carrier into the measuring device.

However, alternatively or additionally, the control device 142 can also be configured as a data manager and can be coupled to a separate blood glucose measuring device. Said separate blood glucose measuring device can then be introduced into the medical system 144 by means of a conventional technique or else by means of a corresponding plug-and-play technique, for example in accordance with the method according to the invention.

A plurality of complete data records concerning medical user elements 140, for example concerning disposable-reusable systems, can be stored in the control device 142, where they can be temporarily correlated for example by means of real-time data, the blood glucose data and further events. The data records can be read out and, if appropriate, processed further wholly or in part, likewise for example by means of a computer authorized in a plug-and-play step, for example the PC system 168 in FIG. 9.

As explained above, the medical user element 140 preferably does not have its own actuator system and/or input/output interface, for example its own display, for directly signaling to the user 122 states which then, if appropriate, are interpreted by said user or even should be interpreted by said user. Thus, it is desired if the medical system 144 ensures to an increased extent and actively that faults do not lead to incorrect measurement values. This can be realized for example substantially by means of so-called "failsafe" functions, for example with sensor electrode monitoring, monitoring with regard to contact interruption, monitoring of the operating voltages, monitoring of signal patterns or similar fault monitorings. If the medical system 144 is still operational in terms of its basic functions, for example with regard to the signal detection by means of the sensor 110 (for example an optical and/or electrochemical analyte detection), a voltage supply or telemetry, then it is possible to store the states of the medical user element 140, for example of the sensor 110, together with the data records of the personal data, for example in the data memory 132 and/or the data memory 134. This status, if appropriate together with the personal data, for example the data record and/or curve progression 172, can then be stored, transmitted to the control device 142 and also represented there, if appropriate, on the indicator element. Since, however, in particular the instant of the wireless data transmission does not have to be close to the time of the actual event which led to the recording of the data record and/or curve progression 172, or to the point in time of a malfunction, for example measurement data beset with fault messages in the status can be excluded from an indication. If appropriate, advice can also be issued to a user, for example once again by means of the indicator element 182.

In the broadest sense, additional monitoring can also be performed under the plug-and-play method described above. Thus, monitoring of a proper fit of the sensor 110, for example of a sensor/patch unit, could also be effected, for example proper adhesion of the sensor plaster 126 on a skin surface of the user 122. This is to be advocated particularly when long-term sensors 110 are used which are intended to yield measurement results for example over a week or longer. In this way, by way of example, a sensor insertion site and/or a skin region beneath the sensor plaster 126, which generally cannot be seen from outside, can be monitored and abnormal states can for example be detected and, if appropriate, reported or communicated to a user 122. This could be done for example by means of an optical and/or thermal sensor system that is separate or integrated in the sensor 110. The data of said sensor system can also be contained in the personal data and become concomitantly communicated to the control device 142. In this way, the control device 142 can issue corresponding warnings, for example, to the user.

Thus, embodiments of the medical system having plug-and-play function are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. A medical system for monitoring and/or controlling at least one bodily function of a user, comprising:
   a blood glucose measuring device;
   at least one additional device, wherein either the blood glucose measuring device or the additional device or both serve as a control device; and
   at least one medical user element embodied separately from the control device and configured to perform a medical function,
   wherein the medical user element and the control device are configured to exchange data wirelessly,
   wherein the medical user element and the control device are configured to move with respect to each other,
   wherein the medical system is configured to perform an assignment coupling between the control device and the medical user element using a coupling interface and without physical contact between the control device and the medical user element;
   wherein the control device and the medical user element exchange personal data automatically via a wireless communication link, wherein the personal data is exchanged only in response to the assignment coupling;
   wherein a data exchange between the medical user element and the control device that are assigned to one another is effected upon establishment of proximity between the medical user element and the control device so that the data, including the personal data, is transmitted during a time period within which the medical user element moves past the control device.

2. The medical system of claim 1, wherein the control device is configured to be stationary or move at a different speed with respect to the medical user element.

3. The medical system of claim 1, wherein the medical user element is configured to be carried by the user.

4. The medical system of claim 3, wherein the medical user element is configured to be carried directly on or in the body.

5. The medical system of claim 1, wherein the data exchange between the medical user element and the control device is performed at transmission rates of more than 100 kbit/s.

6. The medical system of claim 1, wherein the data exchange between the medical user element and the control device comprises a connection set-up between the medical user element and the control device and a transmission of personal data between the medical user element and the control device.

7. The medical system of claim 1, wherein the personal data are transmitted between the medical user element and the control device by a single or by a repeated exchange of complementary data records.

8. The medical system of claim 1, wherein temporal profiles of measurement values are transmitted between the medical user element and the control device in compartments.

9. The medical system of claim 1, wherein temporal profiles of measurement values are mapped as a function of time over a total observation period.

10. The medical system of claim 1, wherein the medical system is configured in a manner that it firstly communicates a first partial data record wirelessly upon establishment of proximity between the medical device and the control device.

11. The medical system of claim 10, wherein the medical system is configured in a manner that, if time remains during the establishment of proximity, further partial data records are transmitted.

12. The medical system of claim 10, wherein the medical system is configured in a manner that further partial data records are transmitted at later instants upon later instances of establishment of proximity.

13. The medical system of claim 10, wherein temporal profiles of measurement values are represented completely by the first partial data record.

14. The medical system of claim 13, wherein the medical system is configured in a manner that a representation of the temporal profiles of the measurement values become more accurate with communication of at least one further partial data record.

15. The medical system of claim 1 wherein the control device is configured as a data manager.

16. The medical system of claim 1 wherein the control device has at least one measurement function independent of the medical user element.

17. The medical system of claim 1 wherein the medical user element comprises one or more of the following elements,
   a sensor configured to detect at least one analyte in a body fluid that can be implanted into a body tissue;
   a measuring device configured to detect at least one bodily function; and
   an insulin pump, and a medical actuator device comprising at least one actuator for controlling bodily function.

18. The medical system of claim 1 wherein the control device and the medical user element are prevented from exchanging personal data after the assignment coupling is terminated.

19. The medical system of claim 1 wherein the one additional device is further defined as a mobile radio device, a sport device, a personal digital assistant, a smart phone, pulse meter, or a pedometer.

* * * * *